United States Patent [19]
Dennison

[11] Patent Number: 5,109,215
[45] Date of Patent: Apr. 28, 1992

[54] MEANS AND METHOD FOR MONITORING A PROTECTIVE GARMENT

[76] Inventor: Everett Dennison, 200 Glenview, Canfield, Ohio 44406

[21] Appl. No.: 684,551

[22] Filed: Apr. 12, 1991

Related U.S. Application Data

[63] Continuation-in-part of Ser. No. 537,811, Jun. 14, 1990, Pat. No. 5,036,309.

[51] Int. Cl.$^5$ .......................................... G08B 21/00
[52] U.S. Cl. .................................. 340/540; 128/897; 128/898; 128/917; 128/918; 340/605; 606/34
[58] Field of Search ............... 340/540, 647, 604, 605; 606/34; 128/897, 898, 917, 918

[56] References Cited

U.S. PATENT DOCUMENTS

| | | | |
|---|---|---|---|
| 4,583,039 | 4/1986 | Kolcio | 324/557 |
| 4,692,748 | 9/1987 | Pinsak | 340/573 |
| 4,909,069 | 3/1990 | Albin | 73/40 |
| 4,956,635 | 9/1990 | Langdon | 340/540 |

Primary Examiner—Glen R. Swann, III
Attorney, Agent, or Firm—Terry M. Gernstein

[57] ABSTRACT

A protective garment, such as a surgeon's glove, is monitored for the occurrence of a breach in that garment. The monitoring is performed using an improved version of the system disclosed in U.S. Pat. No. 5,036,309, issued Jul. 30, 1991. The system is improved by adding monitors for ensuring that contacts are in proper and secure electrical contact with both the worker and the workpiece. The system is further improved by adding electrical buses so that further contact monitors and garment integrity monitors can be added to the basic system and a start-up system integrity checking system. All monitors include current amplifying elements, such as transistors.

52 Claims, 9 Drawing Sheets

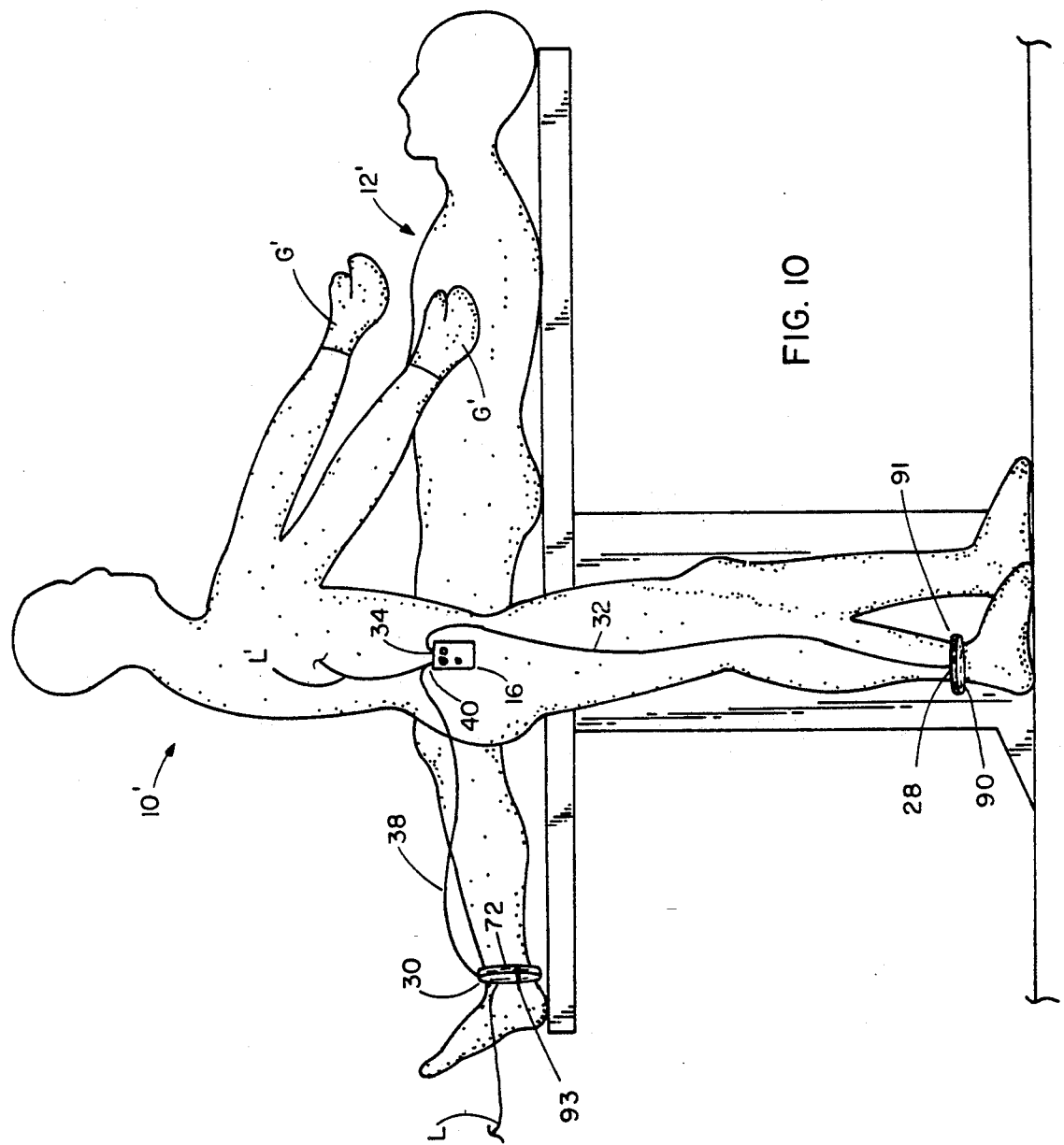

MEANS AND METHOD FOR MONITORING A PROTECTIVE GARMENT

BACKGROUND OF THE INVENTION

The present application is a continuation-in-part of patent application Ser. No. 07/537,811, filed on June 14, 1990, now U.S. Pat. No. 5,036,309, issued July 30, 1991. The disclosure of this parent patent application is incorporated herein by reference.

TECHNICAL FIELD OF THE INVENTION

The present invention relates to the general art of wearing apparel, and to the particular field of protective clothing.

In many industries, a worker may not want any portion of a workpiece to contact any portion of his or her skin. This situation occurs in the chemical industry as well as in several other industries. For this reason, the art contains various examples of protective apparel, such as gloves, aprons, boots, pants, smocks, face shields, gowns and the like.

As more is known of various communicable diseases, more and more workers are using such protective garments in their work. Thus, it is not uncommon to find beauticians or other such workers wearing certain type of protective wearing apparel.

The most notable examples of the use of protective clothing are in the medical and health care field. Thus, nearly all doctors wear some sort of protective apparel when working on a patient. It is not uncommon for dentists to wear protective gloves, masks, gowns, smocks and pants while performing routine examinations and dental procedures. The use of such protection is not limited to doctors, for technicians, nurses, emergency personnel, dental hygienists, and veterinarians are but a few examples of those in the medical field who now commonly wear some sort of protective clothing while carrying out their work. This list is merely representative of the many workers who will benefit from the use of protective clothing, and many other types of workers will occur to those skilled in the art based on the teachings of this disclosure.

Of course, anyone involved in any way with laboratory work in many fields, especially the medical field, almost always wears some sort of protective clothing.

The surgeon and other operating room and hospital personnel are the most visible examples of medical personnel who wear protective clothing while working. Not only do such personnel wear protective clothing to protect a patient from contamination, with the advent of diseases such as hepatitis, AIDS and the like, many such medical workers wear protective clothing to protect themselves from contamination.

While the integrity of all such protective garments must be ensured, the surgical glove has received much attention in the art. One study has found that as much as fifty-nine percent of tested surgical gloves developed leaks when tested every fifteen minutes during surgery, and leakage occurred twenty-five percent of the time when two pairs of gloves were worn. This leakage is probably even higher for certain operations, such as orthopaedic surgery, or the like. Any leakage of the surgical gloves can prove to be dangerous, and should be determined on a regular basis so the medical personnel can be warned upon the occurrence of such a breach.

Therefore, the art has included various procedures which are intended to protect the integrity of the worker's gloves, especially surgical gloves. These procedures have included requirements for a worker to change his gloves at a regular interval, or which require a worker to wear several pairs of gloves. Such procedures are not entirely successful because they interrupt the worker from his work and break his concentration. Furthermore, wearing several pairs of gloves may interfere with proper performance of the task. Even then, as the above-mentioned study found, the worker may not be fully protected.

Thus, the art has also included devices and systems which are intended to detect breaches in a worker's gloves. One such system is disclosed in U.S. Pat. No. 4,321,925. The device disclosed in this patent is intended to continuously monitor a surgeon's gloves to warn of any perforations in those gloves. This device includes a contact on the patient, a contact on the surgeon, and an electrical path through the doctor's shoe, and through the operating room floor to and through the base of the operating table and to and through the table.

While this device overcomes some of the above-mentioned problems, it still has several drawbacks, as discussed in the parent application.

While ensuring the integrity of a worker's gloves is quite important, due to the highly contagious and dangerous nature of many diseases and many chemicals, integrity monitoring of a workers's gloves alone may not be sufficient protection. In many situations, including a surgical operating room, any physical contact with the workpiece may prove to be dangerous.

Therefore, even beyond the drawbacks and problems mentioned for the known glove testers per se, they may have shortcomings in that they do not monitor all of the protective clothing being worn by a worker. Should that worker have a breach in his or her face mask, for example, such breach can be dangerous if the worker must bring his or her face in close proximity to a patient, for example to perform the work, as might be the case of an ambulance worker who must find and grasp a patient's tongue to prevent choking.

Yet another system for monitoring personnel barriers, such as surgical gloves, is disclosed in U.S. Pat. No. 4,956,635. This system includes a pair of comparitors to monitor the integrity of a barrier. This system monitors probes mounted on the doctor and probes mounted on both the doctor and on the patient. A blinking light indicates that the probes are mounted on the doctor, and a steady light indicates that a breach through the doctor's glove has occurred. The status signal of the system is continuously monitored by the health care worker.

While this system is somewhat successful in overcoming some of the problems associated with protective gloves, is still suffers from several drawbacks that may inhibit its full acceptance by health care workers. For example, the use of comparitors by this patented system may create several problems.

For example, a comparitor is a device whose output switches between two possible values depending on the value of the input voltage relative to a reference voltage value. Thus, in the case of the patented system, if the value of voltage applied to the input connection of the comparitor is higher than the value of the reference voltage applied to the reference connection of the comparitor, the comparitor will not generate a triggering signal. On the other hand, if the input voltage drops below the reference voltage, the comparitor will generate a triggering signal. However, such operation provides a range of values that will not trigger the comparitor signal, yet may still be in a problem area. That is, should there be a small leak through a glove, for example, while the voltage applied to the input connection of the comparitor may fall, that voltage may not fall far enough to trigger the comparitor signal. Therefore, a situation may occur in which the worker will want to know of a problem, or of at least a developing problem, yet may not be warned since the problem is not acute enough to trigger the comparitor signal. The system therefore is not accurate and precise and will not produce fully repeatable results thereby vitiating some of the advantages attributed thereto.

Still further, a comparitor may generate false signals, especially if the input voltage is very close to the reference voltage. In such a case, the comparitor may cycle repeatedly as the input voltage reaches and exceeds the reference voltage. Still further, since the comparitor is a voltage-driven device, it may be subject to still other errors due to stray and/or static voltages, induced voltages, voltage surges and transients as well as voltage spikes that occur in the circuit due to various elements that are external to the conditions being monitored. One example of this, might be when certain electrical equipment near the comparitor is turned on. Such equipment may induce a voltage surge in the comparitor that either falsely triggers it or falsely prevents it from triggering. In either case, the results provided by the comparitor may tend to vitiate confidence in the system. If the worker is not fully confident in the operation of the system, that worker may tend to ignore a warning signal when that signal should be heeded.

Still further, a comparitor may not react quickly to a problem. If a surgical glove springs a leak, the surgeon will want to know about it as quickly as possible. A comparitor may not react quickly enough to totally prevent the surgeon's hand from becoming contaminated.

Since a comparitor is a voltage-driven device, yet another problem with comparitors occurs because a patient may be exposed to a voltage. Even though the voltage is not high, if a surgeon touches a patient's vital organ, such as a heart, and any voltage is shunted to his gloved hand from the comparitor, that organ can be damaged.

Yet another problem with comparitors occurs because any current associated with the triggering signal must be amplified in order to operate many signalling devices. For example, if a signalling device includes a coil, the current associated with a comparitor trigger signal may not be sufficient to operate and hold the coil in an operative position.

Still another problem with comparitors is associated with the circuitry that is necessary to operate those devices. If additional workers are involved with a certain procedure, or if additional workpieces are involved, the system disclosed in the U.S. Pat. No. 4,956,635 is not easily modified to accommodate such additional workers or workpieces. In fact, it is likely that such additional workers or workpieces will have to have their own monitoring systems. Such a proliferation of monitoring systems may be expensive and may actually interfere with an on-going operation or procedure. In the case of a surgical procedure, several surgeons, several nurses and several technicians may all be involved with one or more patients. If each of these individuals must have their own monitoring system, the overall operating room may become jammed with the monitoring equipment.

Another problem with the patented system is the need stated in the patent for the worker to continuously monitor the system. This requirement may divert some of the worker's attention from his task. Divided attention from the worker may not be desirable, and may be dangerous in some instances.

Other systems for monitoring a glove require the wearer to immerse his gloved hand into a vat of liquid to conduct an integrity check. As was discussed in the parent application, this requirement is cumbersome and may interrupt a work process. Such interruption of work process may not be desirable, and may inhibit acceptance of the system. Still further, many of these systems use an alarm element connected directly to the circuit. These alarm elements are often resistance-type devices that will emit a weak signal as voltage begins to build up; and will emit a strong signal as voltage increases. The signal is thus not repeatable since there can be a variation in when it becomes loud or strong enough to be detected. Therefore, these systems are subject to being considered inaccurate since one person may hear an audible alarm while others may not hear the alarm depending on the acuteness of the person's hearing and his proximity to the alarm device. Still further, since these systems may depend on the voltage drop across the alarm building up to a predetermined level, the system may not be rapid enough for many purposes.

Therefore, there is a need for a system for continuously monitoring protective clothing to detect any breach in such clothing immediately upon occurrence of such of such breach, and which can be used to monitor all of the protective clothing worn by a worker, and which is adaptable to a wide variety of situations and environments, does not require the worker to stop work to check the integrity of the clothing or of the monitoring network, yet which provides repeatable, accurate and precise results and which is easily transported and stored, and which is easily adjusted, donned and is still inexpensive for use by any number of workers and workpieces.

The system disclosed in the parent application overcomes the problems discussed above, and fulfills the just-mentioned needs. However, even this system can be improved. Specifically, the disclosed system can be improved by adding means to signal if a contact has come out of electrical contact with either the worker or the workpiece whereby the network continuity is assured. Still further, the disclosed system can be improved by adding means for easily expanding the system to simultaneously monitor several workers and several workpieces—without unduly complicating the overall system or adversely affecting the integrity of the system or vitiating the use of the system.

OBJECTS OF THE INVENTION

It is a main object of the present invention to provide a system for continuously monitoring protective clothing to detect any breach in such clothing immediately on the occurrence of such breach.

It is another object of the present invention to improve the system disclosed in the parent application.

It is another object of the present invention to improve the system disclosed in the parent application to warn of any nonsecure contact on either a worker or on a workpiece.

It is another object of the present invention to improve the system disclosed in the parent application to permit the system to be easily expanded to accommodate a plurality of workers and/or a plurality of workpieces.

It is another object of the present invention to provide a system for continuously monitoring protective clothing to detect any breach in such clothing immediately on the occurrence of such breach and to provide a rapid signal of such breach.

It is another object of the present invention to provide a system for continuously monitoring protective clothing to detect any breach in such clothing in a manner that is not susceptible to false signals.

It is another object of the present invention to provide a system for continuously monitoring protective clothing to detect any breach in such clothing in a manner that is not susceptible to interference, especially from external sources.

It is another object of the present invention to provide a system for continuously monitoring protective clothing to detect any breach in such clothing in a manner that is accurate, precise and repeatable.

It is another object of the present invention to provide a system for continuously monitoring protective clothing to detect any breach in such clothing in a manner that will not expose the workpiece to high voltage.

It is another object of the present invention to provide a system for continuously monitoring protective clothing to detect any breach in such clothing in a manner that will not expose the workpiece to voltage associated with a voltage source of the system.

It is another object of the present invention to provide a system for continuously monitoring protective clothing to detect any breach in such clothing in a manner that is not susceptible to stray voltage signals.

It is a specific object of the present invention to provide a system for continuously monitoring protective clothing to detect any breach in such clothing using current-driven elements.

It is another specific object of the present invention to provide a system for continuously monitoring protective clothing to detect any breach in such clothing using transistors.

It is another specific object of the present invention to provide a system for continuously monitoring protective clothing to detect any breach in such clothing using a network that includes buses for connecting further monitoring elements thereto.

It is another object of the present invention to provide a system for continuously monitoring protective clothing to detect any breach in such clothing immediately upon occurrence of such breach and which is adaptable to a wide variety of situations and environments.

It is another object of the present invention to provide a system for continuously monitoring protective clothing to detect any breach in such clothing immediately upon occurrence of such breach and does not require the worker to stop work or divert his attention from his work.

It is another object of the present invention to provide a system for continuously monitoring protective clothing to detect any breach in such clothing immediately upon occurrence of such breach and which is easily transported and stored.

It is another object of the present invention to provide a system for continuously monitoring protective clothing to detect any breach in such clothing immediately upon occurrence of such breach and which is easily adjusted.

It is another object of the present invention to provide a system for continuously monitoring protective clothing to detect any breach in such clothing immediately upon occurrence of such breach and which is inexpensive to manufacture, use and modify.

It is another object of the present invention to provide a system for continuously monitoring protective clothing to detect any breach in such clothing immediately upon occurrence of such breach and which rapidly generates a signal that is repeatably emitted at the same level of breach each time.

SUMMARY OF THE INVENTION

These, and other, objects are achieved by a portable system and method for continuously monitoring protective clothing and which includes contacts that are placed directly on both a worker and on the workpiece and that are connected by a network that rapidly, accurately and repeatable responds to any breach in that clothing and to any errors in the set-up of the network. The network includes a portable unit that can be releasably attached to a worker and which has current-driven elements that generate current immediately upon the occurrence of a breach in the clothing or upon one or more leads becoming non-securely attached to a worker or to a workpiece. Alarm devices are also mounted on the worker-attachable portable unit.

Specifically, the current-driven elements include transistors, and, most specifically, such transistors can be selected to have gains of 25,000. Sensitivity-adjusting means, such as a rheostat-type device or jumper circuits can also be included. The signal element includes an audible and/or a visual element. More specifically, the signal element in one embodiment includes a relay-type element whereby actuation of the alarm is rapid and repeatable and does not depend on a voltage build up in the manner of a resistor-type element.

The electrical leads connecting the contacts to the portable unit are fully insulated, and are connected directly to the worker and to the workpiece. Thus, the overall network is not subject to outside influences which may alter or affect the sensitivity, accuracy or repeatability of the overall device.

Due to the fully insulated and portable nature of the device, it can be used in a wide variety of situations and environments to continuously monitor a large variety of different protective clothing garments for a variety of different workers and workpieces. The device is easily transported and stored, yet is quickly and easily donned by a worker and thus is not likely to interfere with a work procedure, especially in an emergency situation.

The device can be used to monitor any protective clothing worn by a worker in any environment or situation and can do so in a continuous, accurate and repeatable manner and will react quickly and precisely to the occurrence of a problem either with the integrity of the protective clothing or with the connection of the network to either the worker or to the workpiece. The reaction is rapid and can include the use of relays or relay-type devices to operate a variety of signalling or recording devices. The system elements are not susceptible to generating false alarms, and are not likely to expose a worker or a workpiece to high voltage. The system uses transistors that require only a very minimal voltage to switch from a cutoff state to an active or a saturated state. Once in an active state, current associated with the transistor can be quite large as determined by a current gain constant associated with the transistor. Since only minimal voltage is required, a worker or a workpiece is not likely to be exposed to large voltages, and due to the large current gains associated with transistors, devices, such as relays, that may require fairly high currents to operate, can be used in the network.

Still further, reaction times associated with transistors are extremely fast so the network of the present invention can have an extremely fast reaction time. Also, due to the current amplification associated with transistors, the alarm devices can be set to react quickly, surely, and quite accurately. Such alarm devices can be designed to activate only at extremely precise and, perhaps, high, levels of current flow, and to do so in an extremely effective manner.

The portable unit can be encased in a special container and can be worn by the worker in a location that is not likely to expose that portable unit to contact with the workpiece or any portion thereof, while the remaining elements of the network are releasably connected to that portable unit. The remaining elements of the network, including insulated wires and contacts, are relatively inexpensive and thus can be discarded and replaced if exposed to contact with the workpiece. If one of these elements is damaged or contaminated, it is easily and quickly replaced. Thus, for example, in an operating room, if fluids from a patient contact the insulated wires of the device, these wires can simply be discarded after the operation is completed and new wires used without incurring undue expense or time. In an ambulance, spare wires and contacts can be carried in case of damage.

Still further, additional workers and additional workpieces can be added to the monitoring network in a quick and expeditious manner without requiring system modification. The network of the present invention includes a bus from both terminals of the power source associated therewith, and additional worker monitoring circuits and additional workpiece monitoring circuits can simply be connected to an appropriate side of the power source via the appropriate bus. Even with the addition of workers and/or workpieces, the overall accuracy, precision, simplicity and reliability of the monitoring network will not be adversely affected. This feature is especially important in the health care field where several doctors, nurses, and technicians may be involved with a single patient, or one health care provider may be involved with several patients, or several health care providers can be involved with several patients. All patients and health care providers can be connected to a single monitoring network and any breach in any clothing or any misconnection to any patient or to any worker will be quickly, surely and accurately identified.

BRIEF DESCRIPTION OF THE DRAWING FIGURES

FIG. 10 illustrates a surgical application of the device of the present invention.

DETAILED DESCRIPTION OF THE PREFERRED EMBODIMENT OF THE INVENTION

Figure 1:
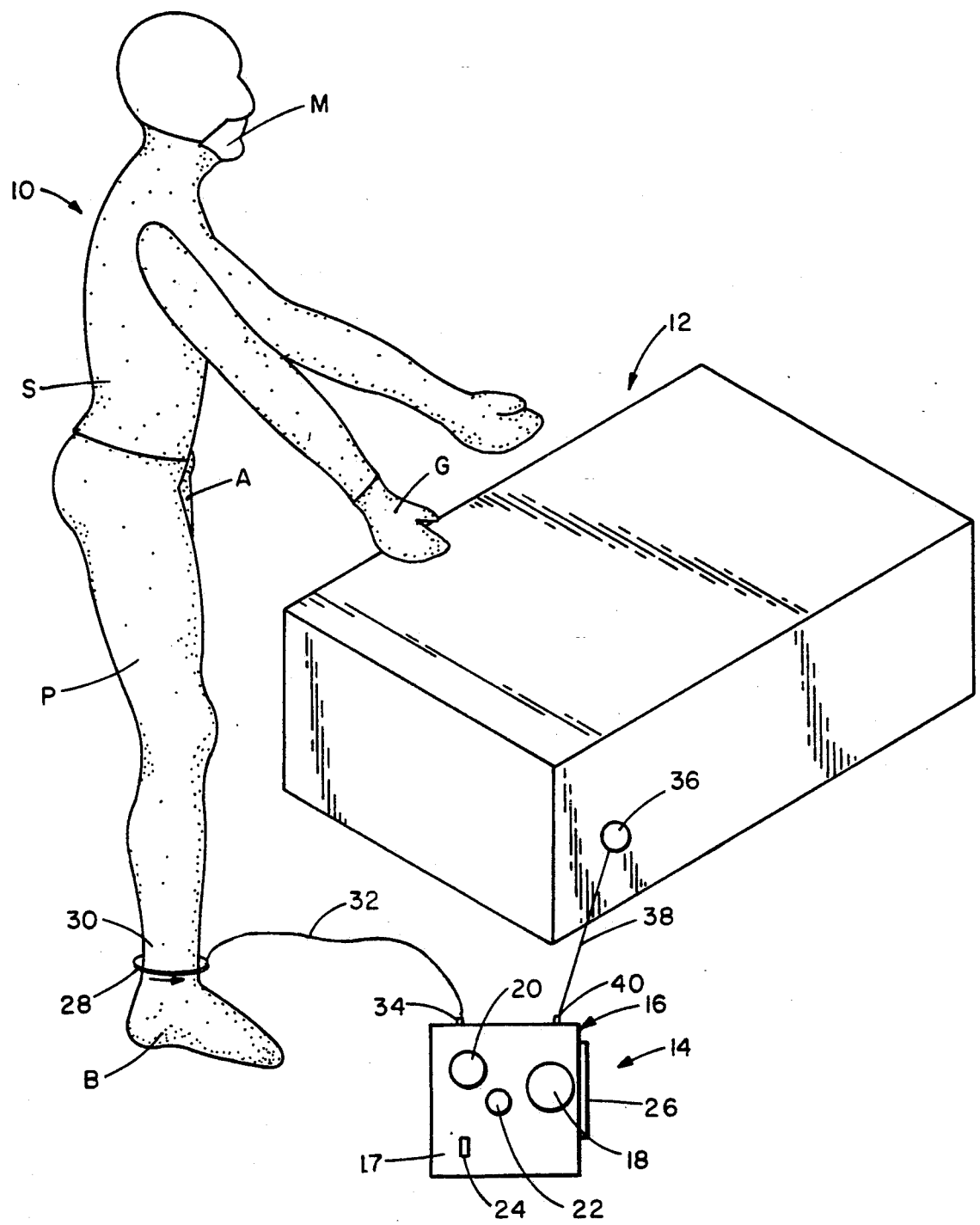
FIG. 1 illustrates the device of present invention connected to a worker and to a workpiece.

Shown in FIG. 1 is a worker 10 carrying out a procedure on a workpiece 12. The workpiece 12 is shown in general block form as it can be an inanimate object, such as a chemical or biological experiment, a quality control operation or the like, as well as an animate object such as a human or an animal. Various applications will occur to those skilled in the art based on the teaching of the present disclosure, and thus the specific examples provided herein are not intended to be limiting, but only examples.

A system 14 is shown in FIG. 1 for electrically connecting the worker 10 to the workpiece 12, and embodies the present invention. The system 14 includes a portable unit 16 having a housing 17 which contains a power source (not shown in FIG. 1), and various circuit elements connecting that power source to an audible alarm element 18 and/or to a visible alarm element 20. A sensitivity-adjusting element 22 and an on/off switch can be used to connect the power source to the remainder of the circuit. A spring-type clip 26 is mounted on the housing to releasably attach the portable unit to the worker as in his pocket, on his belt or the like.

A first electrical contact element 28 is electrically attached to the worker in a location that will not interfere with his work, as on his ankle 30, or the like, and is connected to the circuit in the portable unit by a first fully insulated wire 32 that is releasably connected to that circuit via a jack-like connection 34. The electrical contact is in direct, electrical contact with the worker. Suitable means, such as used in connecting EKG electrodes, can be used to attach the contact to the worker or to the workpiece. In fact, one form of the present invention includes EKG electrodes as the contacts to the worker and to the workpiece.

A second electrical contact element 36 is electrically, and directly, connected to the workpiece and is connected to the circuit elements in the portable unit by a second fully insulated electrical wire 38. The second wire is releasably connected to that circuit via a jack-like connection 40.

The worker 10 is shown wearing various items of protective clothing, such as gloves, such as surgical gloves G, boots, such as boot B, a smock or gown S, pants P, an apron A, a face covering such as mask M or the like. As will be understood from the ensuing discussion, the protective clothing worn by the worker is electrically insulating, and prevents electrical contact between the worker and the workpiece, and, hence, the contact 36. However, should any part of the worker contacts any portion of the workpiece in a manner that completes the electrical circuit as via a breach in that protective clothing, there will be electrical contact between the contact elements 28 and 36 thereby completing the circuit and activating the alarm element or elements.

Figure 2:
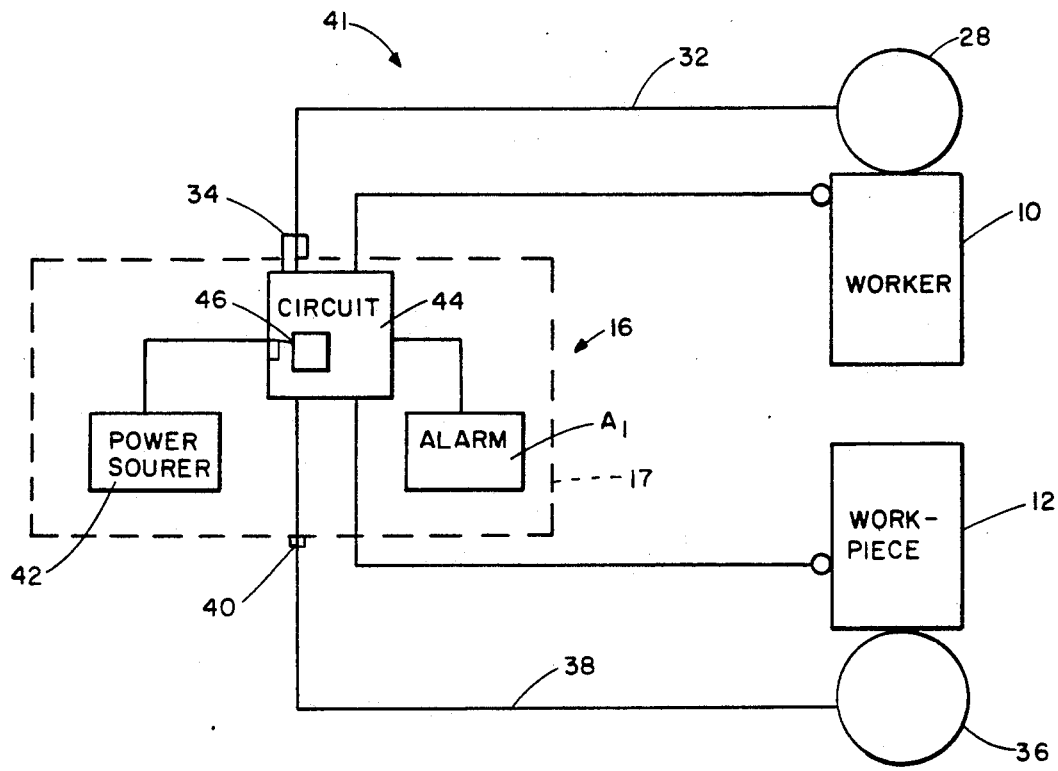
FIG. 2 is a block diagram of the overall system embodying the device of the present invention.

FIG. 2 illustrates the overall network 41 in block diagram form, and shows a power source 42 connected to the circuit 44. The jack-type connections 34 and 40 as well as wires 32 and 38 and the contact elements 28 and 36 are all fully electrically insulated to prevent the overall electrical characteristics of the network 41 from being altered by the influence of outside forces, such as accidental contact with electrically conductive elements or contact with materials that may change their electrical characteristics. Furthermore, such insulation works in conjunction with the other features of the network to prevent false signals from being generated by stray voltage inducing fields of the like in the environment.

Figure 3:
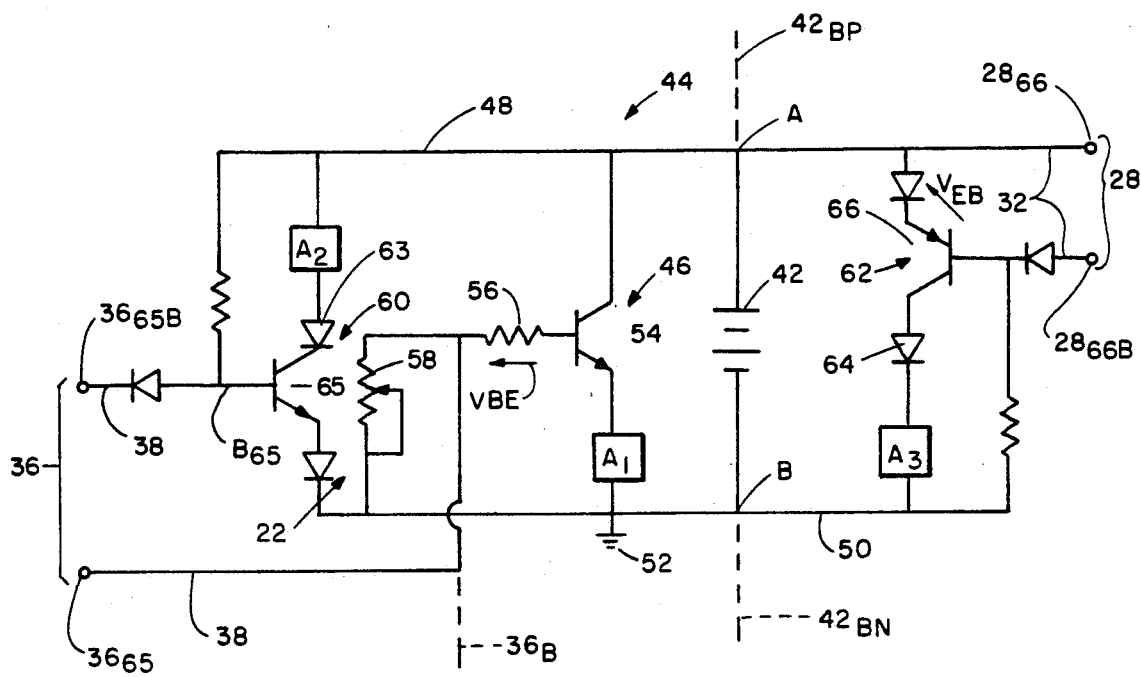
FIG. 3 is a circuit diagram of device of the present invention.
Figure 3A:
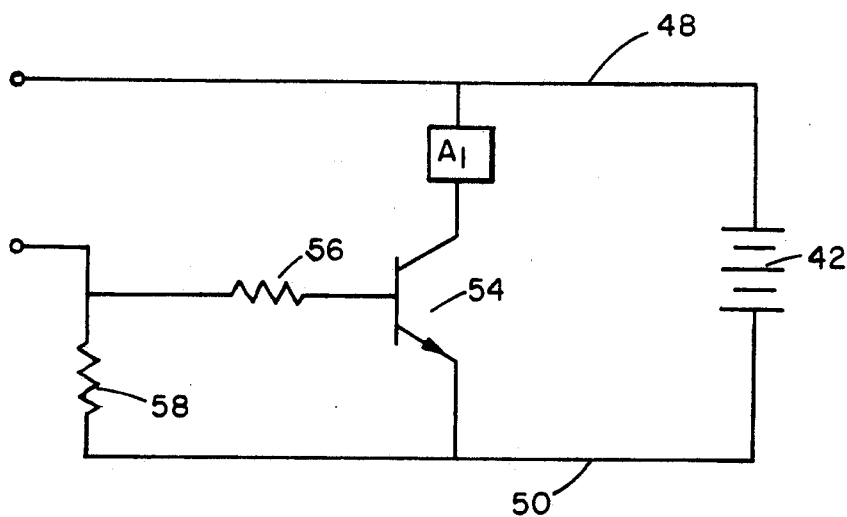
FIG. 3A is a circuit diagram of the device of the present invention in a circuit configuration that occurs when all contacts are securely connected to both the worker and to the workpiece.

The circuit 44 is shown in FIG. 3 as including a current-driven current amplifier device 46 connected to the power source by line conductors 48 and 50 as well as to common point 52. The preferred form of the current amplifier device includes an NPN transistor 54 and has a gain of at least 25,000. A resistor 56 is also included in the circuit. The circuit can also include a sensitivity-adjusting element 22 that includes a rheostate-type device 58. An alarm element and switch are indicated in FIG. 3 as block $A_1$. As discussed in the parent application, this alarm element and switch are activated by current associated with the transistor 54 going into the active state. The alarm and switch $A_1$ will be discussed in greater detail below.

As can be understood from FIG. 3, the contacts 28 and 36 are electrically spaced apart from each other in a normal mode of operation. In such condition, the NPN transistor is biased to have the emitter at negative voltage of the power source whereby the base-emitter voltage ($v_{BE}$) is less than the critical voltage necessary to activate or saturate the transistor, so that transistor is in a cutoff mode. When the transistor is in the cutoff mode, no current flows to the alarm and switch $A_1$, and no power is supplied from the source 42 to the alarm element. However, electrically connecting contacts 28 and 36 places the base of the transistor at a voltage potential higher than the critical voltage with respect to the emitter whereby the transistor goes into an active mode, and generates a quantity of current determined by the current gain of that transistor. Such current can be quite high, and is high enough to activate a coil that might be associated with the alarm element $A_1$, and cause the switch to close thereby completing an electrical path between the alarm elements and the power source to activate such alarm elements.

Figure 3B:
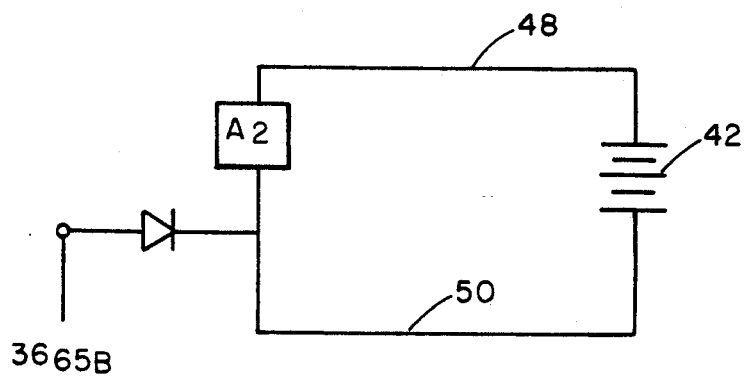
FIG. 3B is a circuit diagram of the device of the present invention in a circuit configuration that occurs when one of the contacts has come loose from the worker.
Figure 3C:
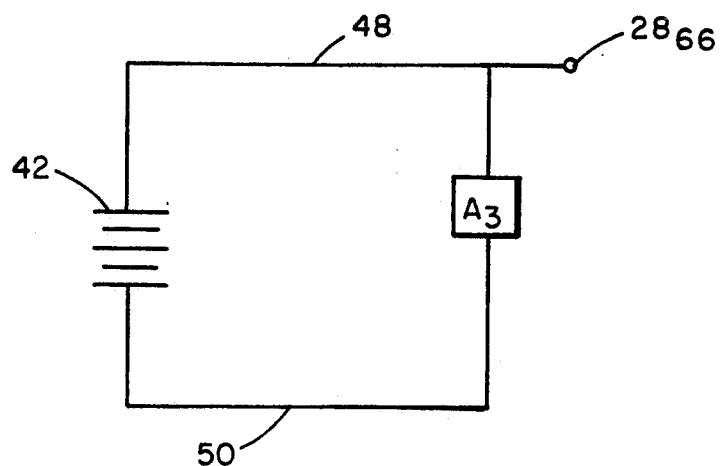
FIG. 3C is a circuit diagram of the device of the present invention in a circuit configuration that occurs when one of the contacts has come loose from the workpiece.
Figure 3D:
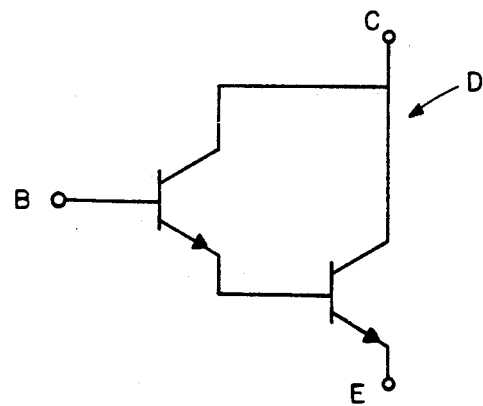
FIG. 3D illustrates a Darlington configuration of two BJT transistors.

The sensitivity of the circuit can be adjusted by element 58 so that the alarm elements will be activated according to the desired amount of current flowing between contacts 28 and 36. The power source can be a nine volt battery or less if suitable. The on/off switch is shown adjacent to the power source, but could be included in any suitable location in the circuit. An alternative form of the amplifier can include a Darlington configuration D as shown in FIG. 3D.

As shown in FIG. 3, the circuit 44 also includes a workpiece contact continuity ensuring circuit 60 having an alarm and switch element $A_2$ therein, and a worker contact continuity ensuring circuit 62 having an alarm and switch element $A_3$ therein. The continuity ensuring circuits are connected to the power source 42 and biased accordingly. The continuity ensuring circuits include transistors that have the emitters thereof connected to the power source and the bases thereof connected to the contact. The transistors are connected in a manner such that when the bases are in electrical contact with the worker or the workpiece, the transistors are biased into the cutoff state, and when one of the contacts comes loose from the worker or from the workpiece the transistor associated therewith is biased into the active state. Each continuity ensuring circuit also includes an LED, such as LED 63 in circuit 60 and LED 64 in circuit 62. These LEDs can emit a visible signal as soon as current moves through the associated transistor.

In the preferred embodiment of the circuit 44, the circuit 60 includes an NPN transistor 65 having the emitter thereof connected to the lead 50 to be connected to the negative side of the power source, and the circuit 62 includes a PNP transistor 66 having the emitter thereof connected to lead 48 to be connected to the positive side of the power source. These configurations biases the transistors so that emitter to base voltages $v_{BE65}$ is less than the critical voltage necessary to drive the transistor 65 into the active state when the base $B_{65}$ is connected to the contact $36_{65}$ via the contact $36_{65B}$ and the workpiece. Likewise, the base voltage to emitter voltage $v_{EB}$ of the PNP transistor 66 will be less than the critical voltage necessary to drive the transistor 66 into the active state when the base $B_{66}$ thereof is connected to the contact $28_{66}$ via the contact $28_{66B}$ and the worker.

However, as soon as one of the contacts $36_{65B}$, $36_{65}$, $28_{66B}$ or $28_{66}$ comes loose, the biasing on the transistor reverses, and exceeds the critical value necessary to drive the transistor into the active state. As soon as the transistor moves into the active state, the LED and alarm system associated therewith receives current, and is activated. Such conditions are indicated in FIGS. 3B and 3C in which contact $36_{65}$ on the workpiece has come loose in FIG. 3B, and contact $28_{66B}$ has come loose from the worker in FIG. 3C. The circuit configurations will be the same the contacts $36_{65B}$ or $28_{66}$ come loose. In any instance, power from the source 42 is applied to the alarm and switch elements. These transistors 65 and 66 can have gains of 25,000 and thus can have a great deal of current associated therewith when they move into the active state so that the alarm and switch elements associated therewith can be selected from a wide range of elements, even those elements that require a great deal of current to operate.

As is also shown in FIG. 3, the circuit 44 further includes a bus $42_{BP}$ connected to the positive side of the power source 42, and a bus $42_{BN}$ connected to the negative side of the power source 42. A further bus $36_B$ is connected to the base of the transistor 54 to permit the further circuits, such as circuit 60, to be added. These buses can be used to connect further contact continuity ensuring circuits and further glove integrity circuits 46 to the same power source 42. One need only attach the additional circuits to the appropriate bus and the single power source 42 can be used to power all of the circuits. Connecting such further circuits to the circuit 44 is quick and easy and does not require a great deal of skill. The additional circuits are identical to the circuits shown in FIG. 3 and all of the elements thereof are identical to those circuits. Therefore, no specific discussion will be presented, and the circuit elements are identified by a prime notation to indicate elements in the additional circuits that are identical to the above-discussed elements in the initial circuits. The various circuits are connected to the basic bus $42_{BN}$ at connections, such as connections A and B.

Figure 3E:
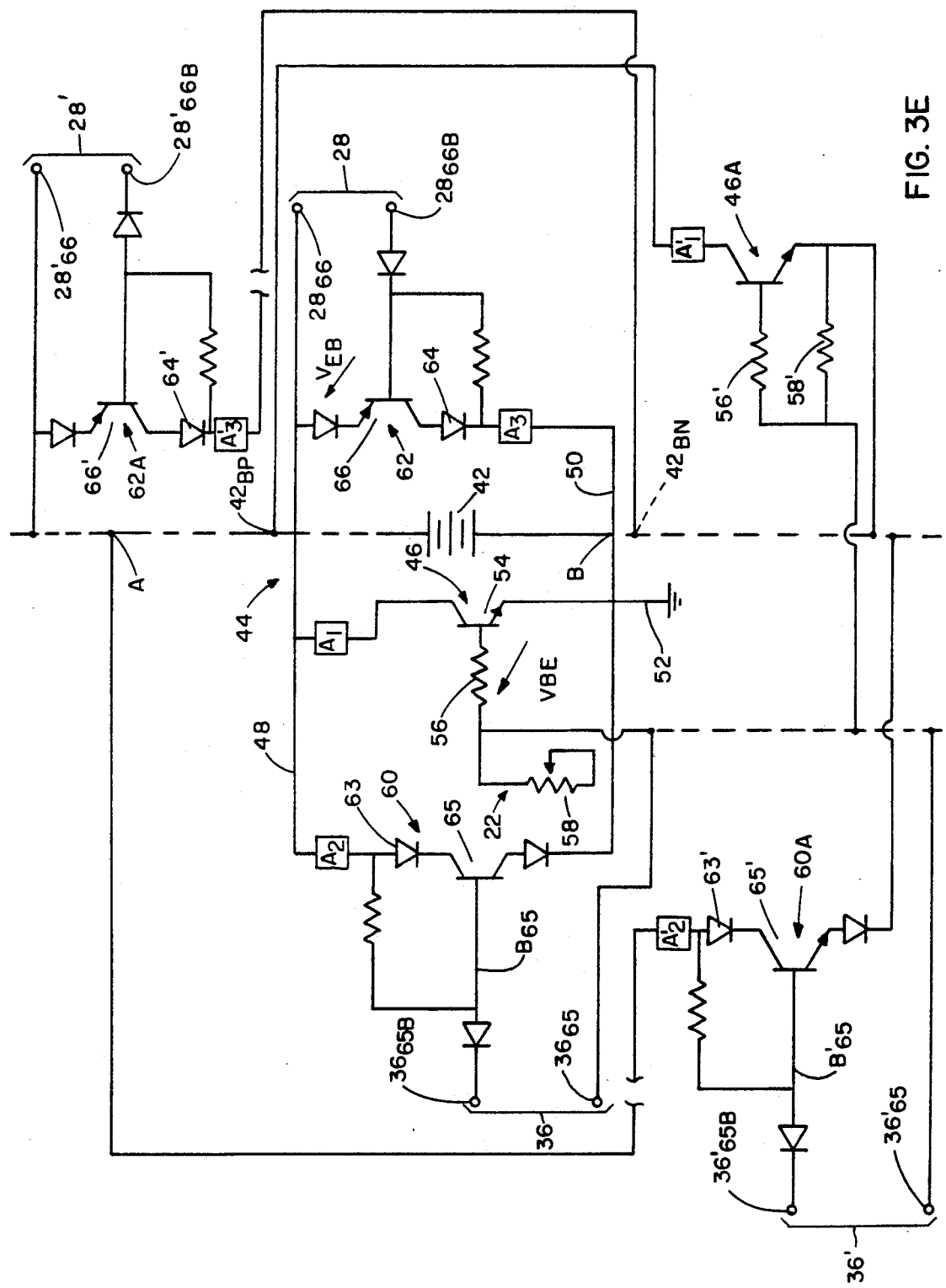
FIG. 3E illustrates the circuit shown in FIG. 3 with additional contact continuity ensuring circuits and an additional glove integrity ensuring circuit connected to a common source via buses.

The additional circuits can be only continuity ensuring circuits, only glove integrity ensuring circuits, or a combination thereof as suitable. An example of such additional circuit connections is illustrated in FIG. 3E in which an additional workpiece circuit 60A is connected to the power source and an additional worker circuit 62A is also connected to the power source.

Figure 4:
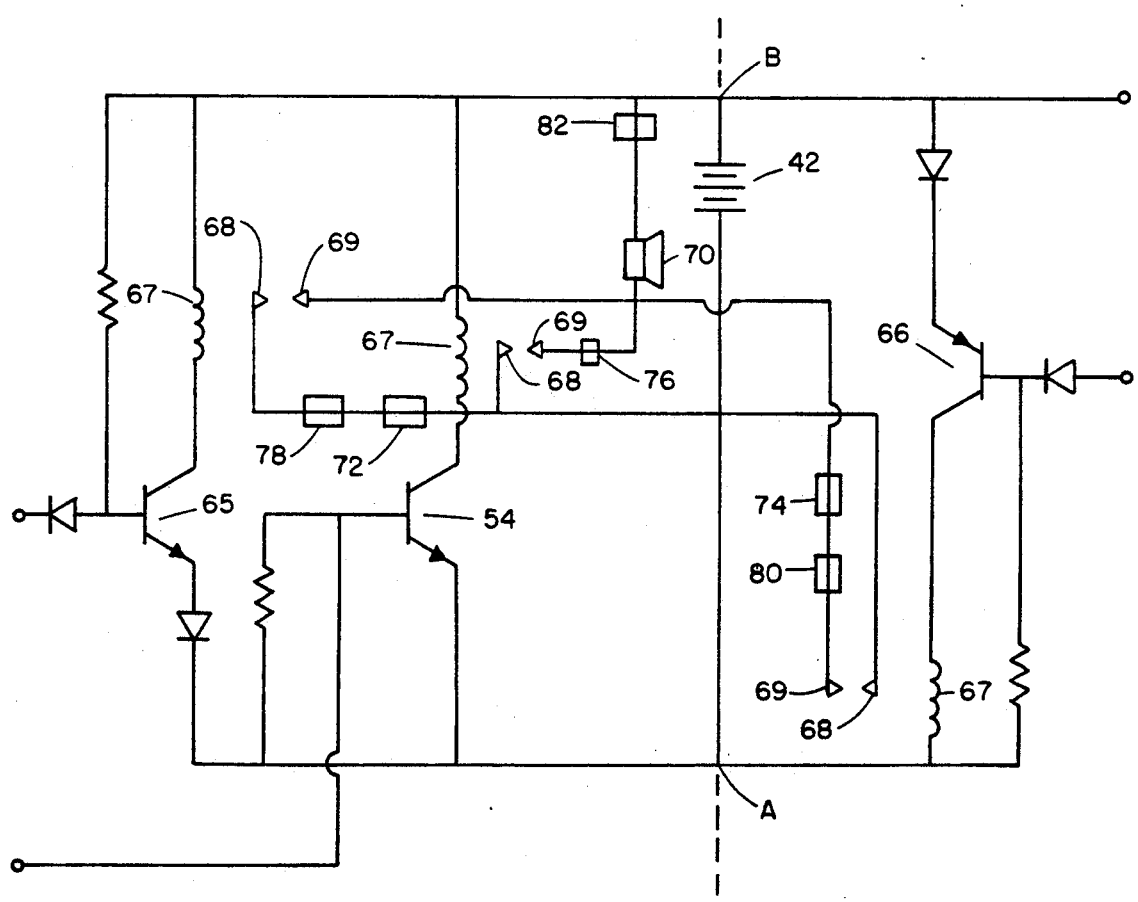
FIG. 4 is a circuit diagram of the device of the present invention in which various alarm elements are included.

The alarm and switch elements can include relays and coils as indicated in FIG. 4. As shown in FIG. 4, a coil 67 is associated with each transistor and receives current as soon as the associated transistor moves into the active state. A contact 68 is associated with each coil 67 and is moved as soon as the coil 67 associated therewith receives current. A second contact 69 is positioned adjacent to the contacts 68, and is contacted by the contact 68 as soon as that contact 68 moves under the influence of the associated coil 67. These contacts are all part of circuits that connect an alarm element, such as a horn 70, to the power source 42 when the contacts 68 and 69 are in electrical contact with each other. Thus, the horn 70 will be activated when any of the transistors 54, 65 or 66 move into the active state. Further alarm indicators, such as lights 72, 74 and 76 can also be included in the alarm circuits. These lights can be various colors so that the workers will immediately know which contact is loose. Still further, circuits, such as circuits 78 and 80 can be included in the alarm circuits to cause the horn 70 to beep when the contacts are loose; whereas, the horn will emit a continuous sound when the glove has been breached. Each alarm and switch element can have its own color or beeping frequency whereby when a plurality of workers or workpieces are being monitored the particular contact that is loose can be identified without requiring all workers or workpieces to be checked. One single horn sound will be used in the preferred embodiment to require all workers to change their gloves if any one of the gloves is breached. This adds an element of security to the overall system. Of course, based on the teaching of the present disclosure, one skilled in the art could add special circuit elements, such as circuit element 82 to emit a special colored light or to cause the horn to sound at a special frequency for certain gloves and different light colors or different frequencies for different gloves. Many forms of relay-type devices can be used if suitable.

Figure 5:
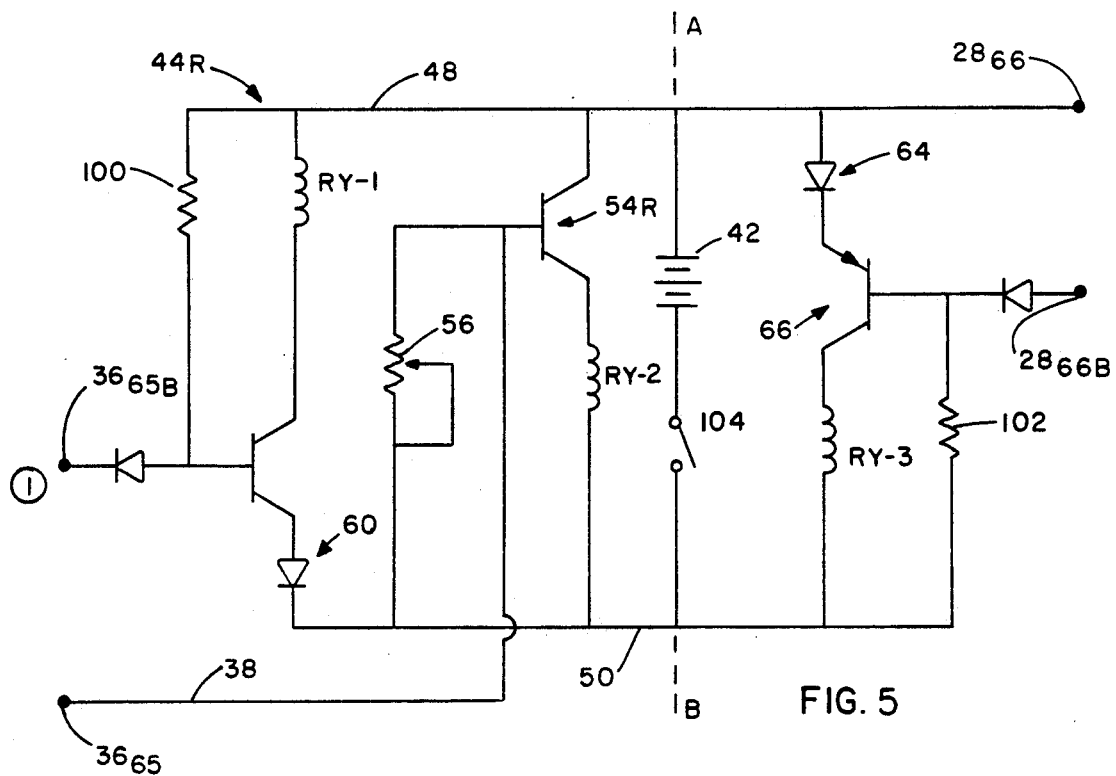
FIG. 5 illustrates an alternative form of the basic circuit shown in FIG. 3.

One alternative form of the basic network is illustrated in FIG. 5 as network 44R, and is similar to the basic network 44. As shown in FIG. 5, resistor 100 is connected between base $B_{65}$ and lead 48, and a relay coil Ry-1 is included in place of alarm $A_2$. Similarly, a resistor 102 is included in the worker-contacting circuit with a relay-type device Ry-3 substituted for alarm $A_3$. The network 44R also includes a relay device Ry-2 connected between the emitter of transistor 54R and lead 50. A manually operated on/off switch 104 connects the power source 42 to lead 50 when closed. In all important respects, the network 44R is similar to network 44 discussed above.

Figure 6A:
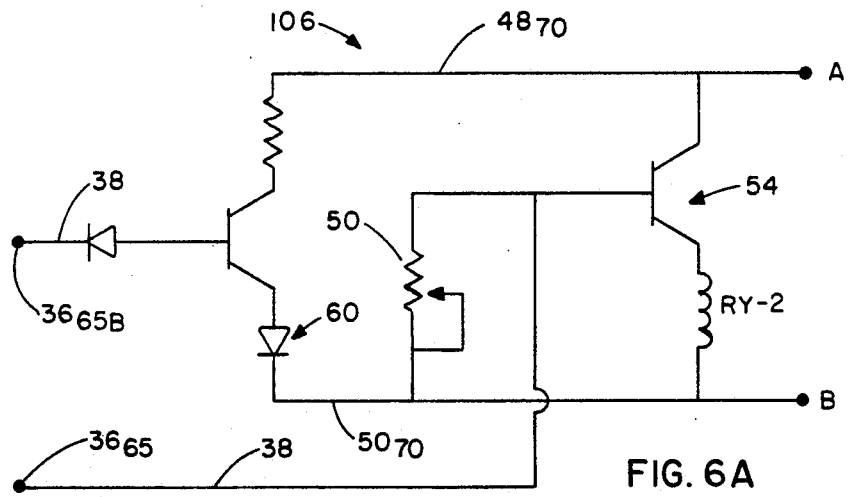
FIG. 6A illustrates an alternative to the workpiece attached circuit shown in FIG. 3.
Figure 6B:
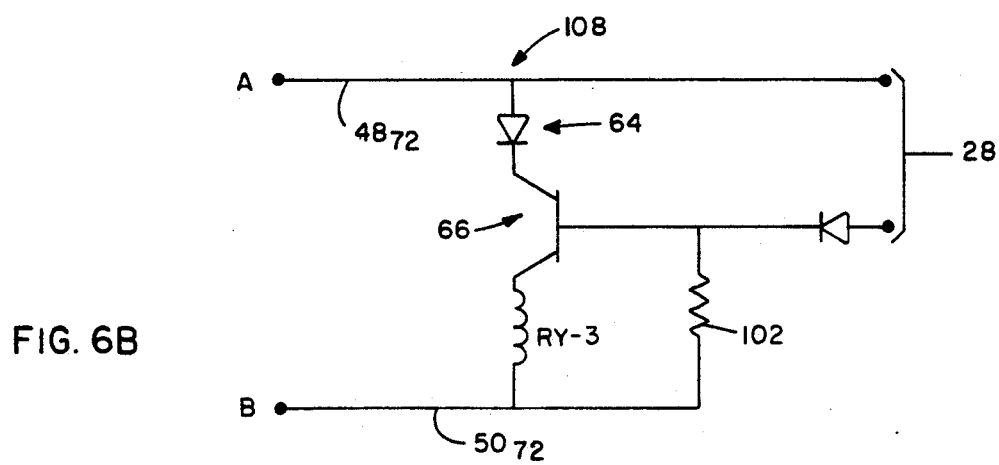
FIG. 6B illustrates an alternative to the worker-attached circuit shown in FIG. 3.

As discussed above, several workers and/or several workpieces can be connected to the same basic network by simply connecting additional circuits to the basic bus $42_{BP}$. A workpiece-attached circuit 106 is illustrated in FIG. 6A, and a worker-attached circuit 108 is illustrated in FIG. 6B. As illustrated in both of these figures, the leads $48_{70}$, $50_{70}$ and $48_{72}$, $50_{72}$ are connected to bus $42_{BN}$ at locations A and B. A combined circuit 44C is shown in FIG. 8 wherein two workpiece monitoring circuits and two worker-monitoring circuits are connected to the basic circuit either by separate leads, such as illustrated in FIG. 8 by leads 110, 112, 114 and 116, or by bus $42_{BN}$.

Figure 7:
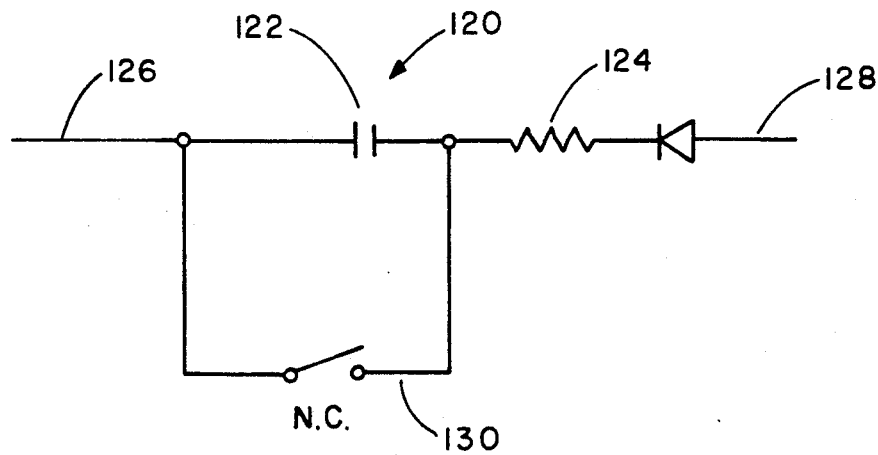
FIG. 7 illustrates a start-up system integrity checking circuit.
Figure 8:
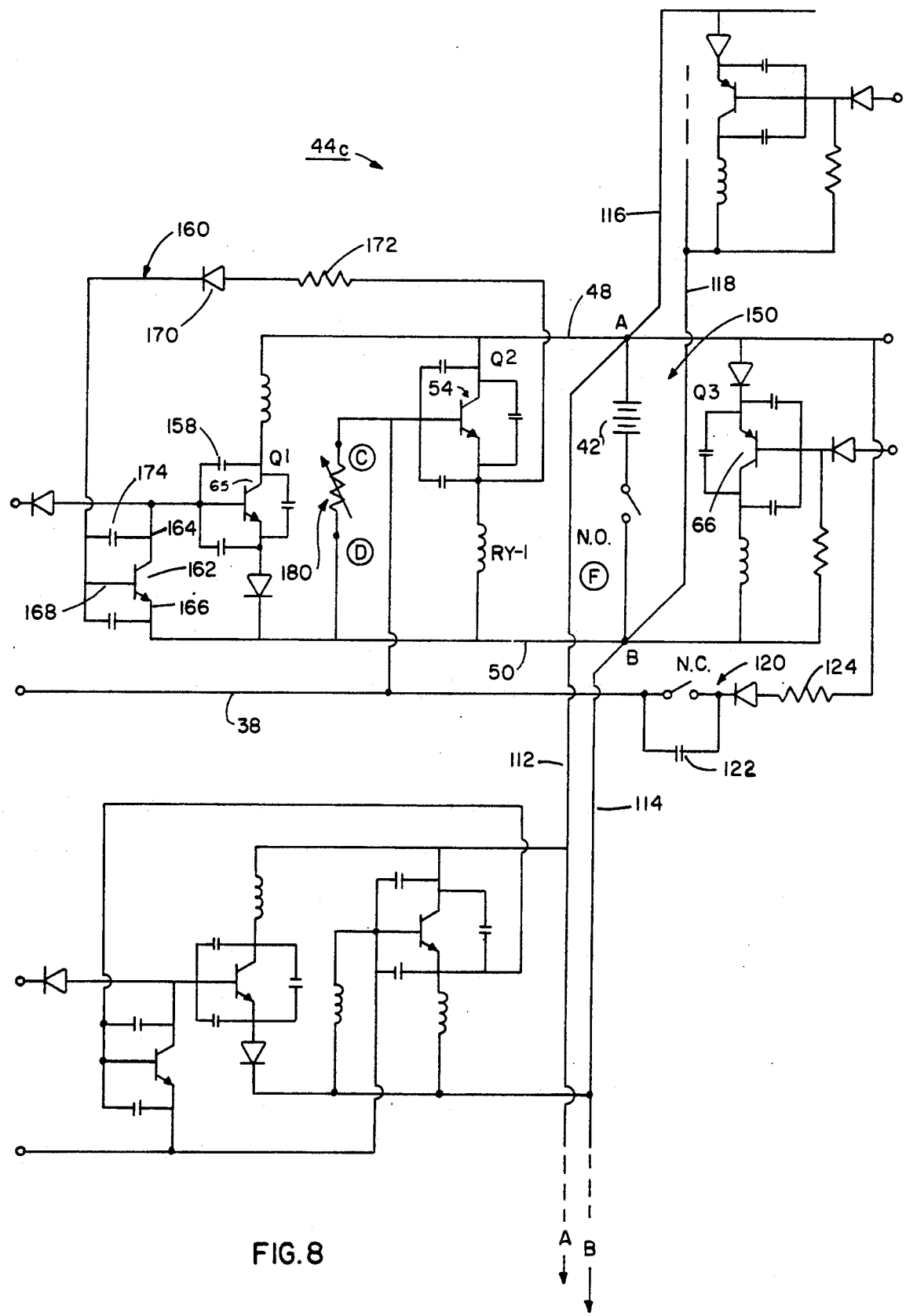
FIG. 8 illustrates an alternative form of the basic network shown in FIG. 3 with a plurality of worker-attached circuits and a plurality of workpiece-attached circuits all combined into one network.

Also illustrated in FIGS. 7 and 8 is a system integrity checking circuit 120. The circuit 120 is activated at start-up and causes the alarm circuit 46 to activate when the on/off switch 104 is initially closed to turn on the system. The circuit 120 includes a capacitor 122 and a resistor 124 and a diode and has leads 126 and 128 connected to contacts $36_{65}$ and $28_{66}$ respectively. A normally closed switch 130 is connected around the capacitor 122. The switch 130 is ganged to the on/off switch 104 to open when switch 104 is closed and to close when switch 104 is open. As can be understood from FIGS. 7 and 8, when the system is in the "off" mode, switch 104 is open and switch 130 is closed. Closing switch 130 causes the capacitor 122 to discharge while the overall network is shut down. However, upon initially activating the network by closing on/off switch 104, the switch 130 opens. The capacitor 122 acts as a short circuit connecting the contact $28_{66}$ to the contact $36_{65}$. This connection causes the alarm circuit 46 to activate thereby generating a signal from alarm element $A_1$. However, the capacitor 130 eventually changes and acts as an open circuit thereby disconnecting the contacts $28_{66}$ and $36_{65}$ to place the overall network in its normal monitoring mode. The time required for the capacitor 122 to open is a function of the RC time constant associated with the capacitor 122 and the resistor 124, and can be set by appropriately selecting these two elements. The initial activation of the alarm circuit indicates that all circuits and power sources are in proper working order.

Figure 9:
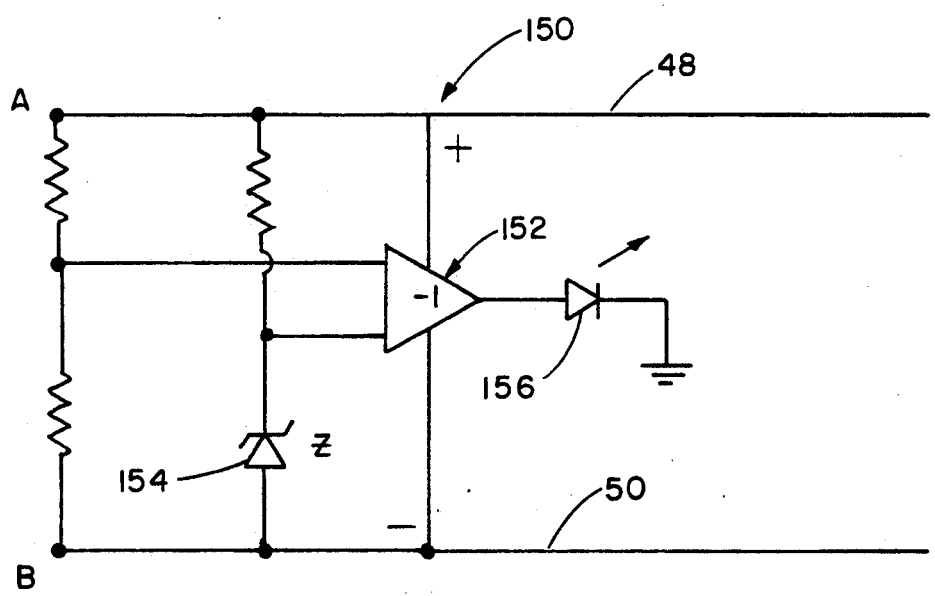
FIG. 9 illustrates a battery monitoring circuit.

A battery monitoring circuit 150 is shown in FIG. 9 and is connected to leads 48 and 50 at locations A and B across power source 42. The monitoring circuit 150 includes a comparitor 152 that compares battery voltage to a reference zenner diode 154. When battery voltage drops below a set level, an LED 156 is activated. An audible signal can be used as well.

It is noted that the circuit 44C shown in FIG. 8 is an alternate form of the basic network and includes a plurality of capacitors, such as capacitor 158, connected around each transistor to prevent RF energy from interfering with the operation of the transistors or the network.

The network 44C also includes a feedback circuit 160 that includes a transistor 162 having the collector 164 thereof connected to the base lead 38, and the emitter 166 thereof connected to lead 50. The base 168 thereof is connected via a diode 170 and a resistor 172 to the transistor 54. Capacitors 174 are also connected around the transistor 162 to prevent RF energy from interfering with the operation of the feedback circuit.

A further alternative of the network includes a variable resistor 180 which is used to adjust the sensitivity of the network. The resistor 180 can also be a jump element that is attached to the circuit as required or replaced as necessary to adjust the sensitivity of the network.

A specific application of the device 14 is shown in FIG. 10 wherein a surgeon 10' is performing surgery on a patient 12'. The surgeon is wearing surgical gloves G' and a disposable cuff 90 is attached to his ankle 30' by hook-and-loop fastening elements 91 and places contact 25 in electrical and direct contact with the surgeon's body. A second disposable cuff 92 is attached to the patient's ankle by a hook-and-loop fastening means 93 or by an EKG-type connector, and places contact 36 in direct and electrical contact with the patient's body. The contacts are connected to the circuit 44 contained in the portable unit 16 that is shown in FIG. 10 as being worn on the surgeon's belt by fully insulated wires 32 and 38 that are releasably connected to the circuit by jack-like connections 34 and 40 as above discussed.

During surgery, the surgeon is required to place his hands onto and inside the patient, as shown in FIG. 10, and thus expose his hands to the body and the bodily fluids of the patient. The circuit 44 monitors the integrity of the gloves so that any breach in the glove will cause the alarm of the circuit to be activated to alert the surgeon of the breach. Furthermore, the circuit 44 alerts the surgeon if the contact on his own body or the contact on the patient comes loose. Should a contact become loose, the circuit 44 will activate the horn, or a beeper or a light or a combination thereof to alert him that the circuit is not properly connected. Obviously, an improperly connected circuit may not properly monitor the gloves, or other apparel, for a breach, and the worker should be notified of such improper connection at the earliest possible time. As above discussed, other workers or other workpieces can be added by simply adding further continuity ensuring circuits to the circuit 44 by connecting such further continuity ensuring circuits to the bus $42_{BP}$ or to the $42_{BN}$.

The sensitivity of the circuit can be adjusted so that any breach or any loss in electrical contact between the contacts and the worker or the patient will complete the circuit. For example, the sensitivity of the circuit can be adjusted so that any breach in the surgeon's gloves which is large enough to permit sufficient quantities of fluid to pass through the gloves as will endanger the surgeon will be large enough to activate the alarm. The inventor has determined that a breach as small as a small pin hole or even as small as one molecule of the workpiece is large enough to permit fluid to penetrate the gloves in quantities sufficient to endanger the surgeon. Therefore, the sensitivity of the circuit can be set so that any fluid from the patient that can flow through a molecule-size hole in the surgeon's gloves and contact the surgeon's skin will be sufficient to activate the alarm elements. However, other opening sizes can be used if desired, even smaller if suitable. The sensitivity can also be adjusted so that a gap between any part of the contact and the worker or the workpiece will cause the alarm elements to be activated.

An additional lead L is also shown connected to the patient whereby additional healthcare workers can be connected to the patient as above described. If there more than one patient, each healthcare worker can be connected to those additional patients, using leads, such as lead L' also as above described.

It is understood that while certain forms of the present invention have been illustrated and described herein, it is not to be limited to the specific forms or arrangements of parts described and shown.

What is claimed is:

1. A system for continuously monitoring a protective garment for detecting and signalling the occurrence of a breach in such protective garment comprising:

A) a unit including
   (1) a housing,
   (2) a power source,
   (3) an alarm device, and
   (4) a circuit for connecting said alarm device to said power source and which includes a current amplifier connected to said power source, said current amplifier having means for generating current when power is applied thereto in a particular manner; and B) normally open switch means for connecting said circuit to said alarm device when closed, said switch means being closed when the person's skin contacts some portion of a workpiece on which that person is working, said switch means including
   (1) a first contact element electrically connected with one side of said power source,
   (2) a second contact electrically connected to one side of said alarm element,
   (3) a current activated element associated with said switch means first contact to cause that switch means first contact to electrically contact said switch means second contact when power is applied to said current activated element in said particular manner to apply power from said power source to said alarm device,
   (4) a first electrical wire connecting another side of said alarm device to another side of said power source,
   (5) a first electrical contact element connected to said power source another side and mountable in electrical contact with the person,
   (6) a second electrical contact element connected to said current amplifier and to said power source one side and being mountable on the workpiece,
   (7) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment, the formation of said electrically conductive path causing power from said power source to be applied to said current amplifier in said particular manner and activating said current amplifier, current associated with said activated current amplifier causing power from said power source to be applied to said alarm device to activate said alarm device.

2. The system for continuously monitoring a protective garment defined in claim 1 wherein said first electrical wire is fully electrically insulated between said first contact element and said circuit.

3. The system for continuously monitoring a protective garment defined in claim 2 wherein said second electrical wire is fully electrically insulated between said second contact element and said circuit.

4. The system for continuously monitoring a protective garment defined in claim 1 wherein said current amplifier element includes a transistor.

5. The system for continuously monitoring a protective garment defined in claim 4 further including a sensitivity adjusting element connected to said power source.

6. The system for continuously monitoring a protective garment defined in claim 5 wherein said sensitivity adjusting element is set so that any perforation in said protective garment will nearly instantly cause said electrically conductive path to be formed so that the integrity of said protective garment is monitored at all times during a work procedure.

7. The system for continuously monitoring a protective garment defined in claim 5 wherein said transistor is an NPN type transistor.

8. The system for continuously monitoring a protective garment defined in claim 5 wherein said sensitivity adjusting element includes a variable resistor.

9. The system for continuously monitoring a protective garment defined in claim 5 wherein said sensitivity adjusting element includes a jump element.

10. The system for continuously monitoring a protective garment defined in claim 5 further including a battery monitoring circuit.

11. The system for continuously monitoring a protective garment defined in claim 10 wherein said battery monitoring circuit includes a comparitor connected to said power source, and a zenner diode connected to said comparitor.

12. The system for continuously monitoring a protective garment defined in claim 4 further including a system start-up integrity checking circuit.

13. The system for continuously monitoring a protective garment defined in claim 12 wherein said integrity checking circuit includes a capacitor connected to said first electrical contact element and to said second electrical contact element and a normally closed switch connected across said capacitor.

14. The system for continuously monitoring a protective garment defined in claim 13 wherein said circuit for connecting said alarm device to said power source further includes a normally open on/off switch connected said power source and to said normally closed switch to open said normally closed switch when said normally open switch is closed and to close said normally closed switch when said normally open switch is open.

15. The system for continuously monitoring a protective garment defined in claim 4 further including a plurality of capacitors connected around said transistor.

16. The system for continuously monitoring a protective garment defined in claim 1 wherein said current amplifying means has a gain of at least approximately 25,000.

17. The system defined in claim 1 wherein said alarm device includes a relay-type device.

18. The system for continuously monitoring a protective garment defined in claim 1 wherein said alarm device includes a relay-type device.

19. The system for continuously monitoring a protective garment for detecting and signalling the occurrence of a breach in such protective garment comprising:

A) a unit including
   (1) a housing,
   (2) a power source,
   (3) an alarm device, and
   (4) a circuit for connecting said alarm device to said power source and which includes a current amplifier connected to said power source, said current amplifier having means for generating current when power is applied thereto in a particular manner;

B) normally open switch means for connecting said circuit to said alarm device when closed, said switch means being closed when the person's skin contacts some portion of a workpiece on which that person is working, said switch means including
   (1) a first contact element electrically connected with one side of said power source,
   (2) a second contact electrically connected to one side of said alarm element,
   (3) a current activated element associated with said switch means first contact to cause that switch means first contact to electrical contact said switch means second contact when current is applied to said current activated element to apply power from said power source to said alarm device,
   (4) a first electrical wire connecting another side of said alarm device to another side of said power source,
   (5) a first electrical contact element connected to said power source another side and mountable in electrical contact with the person,
   (6) a second electrical contact element connected to said current amplifier and to said power source one side and being mountable on the workpiece,
   (7) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment, the formation of said electrically conductive path causing power from said power source to be applied to said current amplifier in said particular manner and activating said current amplifier, current associated with said current amplifier being applied to said normally open switch element and causing said normally open switch element to close, said normally open switch element connecting said power source to said alarm means when closed and causing power from said power source to be applied to said alarm device to activate said alarm device; and C) second current amplifying means for sensing if either said first electrical contact element or said second electrical contact element is not making proper electrical contact with said person or said workpiece respectively.

20. The system for continuously monitoring a protective garment defined in claim 19 wherein said second current amplifying means includes a first transistor element connected to said first electrical contact element.

21. The system for continuously monitoring a protective garment defined in claim 20 wherein said second current amplifying means further includes a second transistor element connected to said second electrical contact element.

22. The system for continuously monitoring a protective garment defined in claim 21 wherein said first transistor element includes an NPN transistor.

23. The system for continuously monitoring a protective garment defined in claim 22 wherein said second transistor element includes a PNP transistor.

24. The system for continuously monitoring a protective garment defined in claim 23 further including an LED element connected to said first transistor.

25. The system for continuously monitoring a protective garment defined in claim 24 further including a second LED element connected to said second transistor.

26. The system for continuously monitoring a protective garment defined in claim 25 further including a second additional alarm means connected to said current amplifying means.

27. The system for continuously monitoring a protective garment defined in claim 19 further including a first additional alarm means connected to said second current amplifying means.

28. The system for continuously monitoring a protective garment defined in claim 19 wherein said second current amplifying means has a gain of at least about 25,000.

29. The system defined in claim 19 wherein said alarm device includes a relay-type device.

30. The system for continuously monitoring a protective garment defined in claim 19 further including a first bus connected to said power source one side and a second bus connected to said power source another side.

31. The system for continuously monitoring a protective garment defined in claim 30 further including a third bus connected to said current amplifier.

32. The system for continuously monitoring a protective garment defined in claim 31 further including further second current amplifying means connected to buses.

33. The system for continuously monitoring a protective garment defined in claim 32 further including a further current amplifier connected to said buses.

34. The system for continuously monitoring a protective garment defined in claim 33 further including additional alarm means connected to said further second current amplifying means.

35. The system for continuously monitoring a protective garment defined in claim 34 further including further additional alarm means connected to said further second current amplifying means.

36. The system for continuously monitoring a protective garment defined in claim 19 further including a feedback circuit connected to said alarm device and to said first electrical wire.

37. The system for continuously monitoring a protective garment defined in claim 36 wherein said feedback circuit includes a transistor connected to said alarm device.

38. The system for continuously monitoring a protective garment defined in claim 37 further including a plurality of capacitors connected around said feedback circuit transistor.

39. The system for continuously monitoring a protective garment defined in claim 38 further including a diode and a resistor connected in series with each other and between said feedback circuit transistor and said alarm device.

40. The system for continuously monitoring a protective garment for detecting and signalling the occurrence of a breach in such protective garment comprising:

A) a unit including
  (1) a housing,
  (2) a power source,
  (3) an alarm device having one side thereof connected to one side of said power source, and
  (4) means for connecting said alarm device to said power source and which includes a current amplifier that acts as an open circuit when power is applied thereto in a first biasing direction and acts as a current generator when power is applied thereto in a second biasing direction, said current amplifier having one side thereof connected to another side of said alarm device, another side of said current amplifier being connected to another side of said power source;

B) a first contact element connectable to a worker and being connected to said power source one side;

C) a second contact element connectable to a workpiece and being connected to said current amplifier element and to said power source another side; and D) said current amplifier and said power source being selected so that said current amplifier is biased in said first biasing direction when said first and second contact elements are electrically separated from each other, and is biased in said second biasing direction when said first and second contact elements are in electrical contact with each other, said alarm device being activated by current generated by said current amplifier element when said amplifier element is biased in said second biasing direction.

41. The system for continuously monitoring a protective garment defined in claim 40 further including an electrically insulating protective garment interposed between said first contact element and said second contact element.

42. The system for continuously monitoring a protective garment defined in claim 41 wherein the workpiece is electrically conductive, and makes electrical contact between said first and second contact elements via a perforation in said protective garment.

43. The system for continuously monitoring a protective garment defined in claim 40 including means for connecting a plurality of workers to said alarm device.

44. The system for continuously monitoring a protective garment defined in claim 43 including means for connecting a plurality of workpieces to said alarm device.

45. The system for continuously monitoring a protective garment defined in claim 40 including means for connecting a plurality of workpieces to said alarm device.

46. A method of monitoring a protective garment comprising steps of:
   A) placing a first electrical contact on a workpiece;
   B) placing a second electrical contact on a worker;
   C) electrically insulating the worker-mounted second electrical contact from the workpiece-mounted first electrical contact using an electrically insulated protective garment;
   D) providing a power source;
   E) providing an alarm;
   F) electrically connected the second electrical contact to one side of the power source;
   G) electrically connecting one side of the alarm to the power source one side;
   H) providing a current amplifier that acts as an open circuit when power is applied thereto in a first biasing direction and acts as a current generator when power is applied thereto in a second biasing direction;
   I) electrically connecting one side of the current amplifier to another side of the power source;
   J) electrically connecting another side of the current amplifier to another side of the alarm;
   K) electrically connecting the first electrical contact to the current amplifier and to the power source another side and biasing the current amplifier in the second biasing direction when the second electrical contact is electrically connected to the first electrical contact and biasing the current amplifier in the first biasing direction when the second electrical contact is electrically insulated from the first electrical contact;
   L) electrically connecting the first electrical contact to the second electrical contact through any perforation occurring in the protective garment; and
   M) activating the alarm using current generated by the current amplifier when the current amplifier is biased in the second biasing direction.

47. The method of monitoring a protective garment defined in claim 46 further including a step of providing the current amplifier with a gain of at least 25,000.

48. The method monitoring a protective garment defined in claim 47 further including a step of adjusting the sensitivity of the current amplifier.

49. The system for continuously monitoring a protective garment for detecting and signalling the occurrence of a breach in such protective garment comprising:
   A) a unit including
      (1) a housing,
      (2) a power source,
      (3) an alarm device, and
      (4) a circuit for connecting said alarm device to said power source;
   B) normally open switch means for connecting said circuit to said alarm device when closed, said switch means being closed when the person's skin contacts some portion of a workpiece on which that person is working, said switch means including
      (1) a first contact element electrically connected with one side of said power source,
      (2) a second contact element electrically connected to one side of said alarm element,
      (3) a first electrical wire connecting another side of said alarm device to another side of said power source,
      (4) a first electrical contact element connected to said power source another side and mountable in electrical contact with the person,
      (5) a second electrical contact element connected to said current amplifier and to said power source one side and being mountable on the workpiece,
      (6) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment; and
   C) means for connecting a plurality of workers to said alarm device.

50. The system for continuously monitoring a protective garment defined in claim 49 further including means for sensing if either said first electrical contact element or said second electrical contact element is not making proper electrical contact with said person or said workpiece respectively.

51. The system for continuously monitoring a protective garment for detecting and signalling the occurrence of a breach in such protective garment comprising:
   A) a unit including
      (1) a housing,
      (2) a power source,
      (3) an alarm device, and
      (4) a circuit for connecting said alarm device to said power source;
   B) normally open switch means for connecting said circuit to said alarm device when closed, said switch means being closed when the person's skin contacts some portion of a workpiece on which that person is working, said switch means including
      (1) a first contact element electrically connected with one side of said power source,
      (2) a second contact element electrically connected to one side of said alarm element,
      (3) a first electrical wire connecting another side of said alarm device to another side of said power source,
      (4) a first electrical contact element connected to said power source another side and mountable in electrical contact with the person,
      (5) a second electrical contact element connected to said current amplifier and to said power source one side and being mountable on the workpiece,
      (6) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment; and C) means for connecting a plurality of workpieces to said alarm device.

52. The system for continuously monitoring a protective garment defined in claim 51 further including means for sensing if either said first electrical contact element or said second electrical contact element is not making proper electrical contact with said person or said workpiece respectively.

* * * * *